United States Patent
Conlan et al.

[11] Patent Number: 5,904,147
[45] Date of Patent: May 18, 1999

[54] INTRAVASCULAR CATHETER AND METHOD OF CONTROLLING HEMORRHAGE DURING MINIMALLY INVASIVE SURGERY

[75] Inventors: A. Alan Conlan, Worcester; Yuri E. Kazakevich, Andover; Steven W. Ek, Bolton; Gheorghe Mihalca, Chelmsford, all of Mass.

[73] Assignees: University of Massachusetts, Worcester, Mass.; Smith & Nephew Endoscopy, Inc., Andover, Mass.

[21] Appl. No.: 08/696,572

[22] Filed: Aug. 16, 1996

[51] Int. Cl.⁶ .................................................. A61B 19/00
[52] U.S. Cl. ........................... 128/899; 604/96; 604/914; 600/146; 600/182
[58] Field of Search ........................ 604/99–101, 20–21; 606/2, 15, 191–194, 111; 600/113–117, 129, 160, 178–179, 12, 182, 146, 424, 585; 607/88, 90; 128/899

[56] References Cited

U.S. PATENT DOCUMENTS

| | | | |
|---|---|---|---|
| Re. 34,544 | 2/1994 | Spears | 604/20 |
| 4,063,561 | 12/1977 | McKenna . | |
| 4,345,588 | 8/1982 | Widder et al. | 600/12 |
| 4,384,584 | 5/1983 | Chen . | |
| 4,512,762 | 4/1985 | Spears | 604/21 |
| 4,655,746 | 4/1987 | Daniels et al. . | |
| 4,671,287 | 6/1987 | Fiddian-Green . | |
| 4,773,899 | 9/1988 | Spears | 604/20 |
| 4,777,951 | 10/1988 | Cribier et al. . | |
| 4,798,588 | 1/1989 | Aillon . | |
| 4,961,738 | 10/1990 | Mackin | 606/15 |
| 4,998,930 | 3/1991 | Lundahl | 606/15 |
| 5,007,919 | 4/1991 | Silva et al. | 606/194 |
| 5,019,075 | 5/1991 | Spears et al. . | |
| 5,259,837 | 11/1993 | Van Wormer | 604/96 |
| 5,324,260 | 6/1994 | O'Neill et al. | 604/96 |
| 5,370,640 | 12/1994 | Kolff | 606/2 |
| 5,395,331 | 3/1995 | O'Neill et al. | 604/96 |
| 5,409,483 | 4/1995 | Campbell et al. . | |
| 5,542,938 | 8/1996 | Avellanet et al. . | |
| 5,562,657 | 10/1996 | Griffin . | |
| 5,645,562 | 7/1997 | Haan et al. | 606/194 |
| 5,700,243 | 12/1997 | Narciso, Jr. . | |
| 5,722,426 | 3/1998 | Kolff . | |
| 5,738,652 | 4/1998 | Boyd et al. . | |

FOREIGN PATENT DOCUMENTS

| | | | |
|---|---|---|---|
| 0283661 | 9/1988 | European Pat. Off. . | |
| 000363117 | 4/1990 | European Pat. Off. | 604/100 |
| 0422690 | 4/1991 | European Pat. Off. . | |

*Primary Examiner*—Mickey Yu
*Assistant Examiner*—Kelly O'Hara
*Attorney, Agent, or Firm*—Lahive & cockfield, LLP

[57] ABSTRACT

A catheter, for example a balloon or treatment catheter, is positioned to prevent hemorrhage during surgery by inserting the catheter in a deflated configuration along a passage such as a blood vessel near to the operative site in a position determined by direct or video-assisted viewing from outside the passage. In the event a blood vessel is cut during surgery, the previously positioned catheter inflates a balloon to occlude the passage and stop blood flow into the injured site. A flow-directed catheter includes an inflatable balloon attached at its distal end and an optical fiber connected to one or more light emitting regions positioned in the vicinity of the balloon. The light is emitted transversely, and preferably omnidirectionally at one or more points with a sufficient brightness to provide beacons that are readily detected through the walls of a blood vessel and permit a direct determination of the exact location of the balloon within the vessel. Rather than a flow-directed balloon catheter, a drug-delivery or other catheter may be used. In that case the light emitting regions are located at or adjacent to one or more drug delivery ports or other active areas in the catheter.

9 Claims, 5 Drawing Sheets

INTRAVASCULAR CATHETER AND METHOD OF CONTROLLING HEMORRHAGE DURING MINIMALLY INVASIVE SURGERY

BACKGROUND OF THE INVENTION

This invention relates to intravascular catheters, and more particularly to balloon-tipped catheters and to a novel method of use to control hemorrhage during surgery.

Minimally invasive or video-assisted surgical procedures are being rapidly developed as a method of replacing conventional surgery. These new techniques reduce surgically-induced complications and subsequently, the medical costs associated with long hospital stays. Current minimally invasive surgical techniques include laparoscopic, endoluminal, perivisceral, endoscopic, thoracoscopic, intra-articular and hybrid approaches. As an illustration of this procedure, access into a body cavity, e.g., peritoneal or pleural cavity, is made through a small incision. The cavity may be insufflated with gas, such as carbon dioxide or saline fluid to provide a working space, if necessary, as is commonly done for laparoscopic or intra-articular procedures, in which case the gas or fluid is injected through an insufflation needle. After removing the needle, surgical instruments may be inserted at the incision into the cavity or working space, and an endoscopic camera is inserted through the opening into the cavity. Under direct visualization, additional incisions are then made at strategic locations in the body for inserting secondary surgical instruments to perform the operation.

Despite the significant advances in minimally invasive techniques, serious complications may arise due to accidental cutting or perforation of vessel or organ. As an illustration, the application of these techniques to pulmonary resections, particularly lobectomy or partial lobectomy, has been limited by the fear that the pulmonary artery is relatively inaccessible, so that hemorrhage, if it occurs, cannot be easily stopped in a closed chest. Currently, the routinely used method of controlling hemorrhage in a closed space is to apply a clip or staple to the injured vessel. This would be a difficult undertaking once hemorrhage commences due to the lack of visibility at the operative site in a closed cavity.

Therefore, a need exists for an effective manner of stopping vascular flow into an operative site during a minimally invasive surgical procedure, particularly in thoracoscopic applications.

The use of balloon-tipped catheters which are flow-directed to the pulmonary artery for measuring right-sided vascular pressures was first described in 1953 (Lategola, M. and Rahn, H. (1953) Proc. Soc. Exp. Biol. Med. 84: 667–68). Since then, pulmonary artery balloon catheters have been widely used for monitoring vascular pressures in the fields of anesthesia and critical care medicine. In 1970, Swan, Ganz and associates reported the use of a flow-directed catheter in humans and further refined it for direct measurement of pulmonary capillary wedge pressure (Swan et al. (1970) N Engl J Med 283: 447–51). At present, this catheter is an invaluable aid in the management of critically ill patients with pulmonary and cardiac disease. Moreover, pulmonary wedge pressure (as an estimation of left ventricular filling pressure or preload) is the standard of reference for intravascular volume management.

In addition to monitoring right heart pressures, balloon-tipped catheters, particularly flow-directed Swan-Ganz catheters have been routinely used for sampling mixed venous blood, and for infusing solutions. Numerous variations of these catheters are available in configurations containing double and triple lumens, as described in U.S. Pat. Nos. 3,746,003, 3,833,004, 3,710,781, 3,634,924, 3,152,592, 3,044,468, 3,050,066 and 2,845,930 and elsewhere.

Balloon-tipped catheters are generally inserted under pressure waveform monitoring, with or without fluoroscopic control. Typically, the catheter may be inserted into a patient at the bedside into a median basilic or deep brachial vein by a cutdown, or it may be inserted percutaneously through the subclavian, internal jugular or femoral vein. After insertion, the balloon on the catheter tip is carried by the stream of maximal blood flow through the right atrium and right ventricle into the branch of the right pulmonary artery and, with a lesser frequency, into the left pulmonary artery. Variations on the ultimate location of the catheter depend mainly on the position of the patient when the catheter is inserted (Parlow, J. L. (1992), J. Cardiothoracic and Vascular Anesthesia 6(1):20–23), but surgeons also develop their own movements for steering to a desired site.

A primary objective of the present invention is to provide a modified balloon-tipped flow-directed catheter useful for stopping the blood flow in the event of injury to a vessel during minimally invasive surgery.

If such a catheter could be dependably and quickly deployed in a determined position by a vessel branch point, it could be used intraoperatively to provide emergency hemostasis.

It is thus an object of the invention to provide a balloon catheter that is readily deployed during endoscopic surgery at a site effective to occlude a vessel supplying the site of surgery.

It is a further object to provide a method of quickly and efficiently deploying such balloon, and method of stopping hemorrhage with the balloon.

It is also an object of the invention to provide a balloon-tipped catheter containing a light fiber positioned in the balloon assembly which emits light in the vicinity of the balloon.

Another object is to provide a method of controlling hemorrhage during minimally invasive surgery, such as thoracic surgery, wherein the balloon catheter of the present invention is inserted into the pulmonary artery on the side of the lung to be operated on and the exact location of the balloon is determined by direct visual or video observation of emitted light. In the event of injury to the vessel during surgery, the balloon is inflated to stop the blood flow.

It is more generally an object of the invention to provide an endovascular catheter and a method of positioning the catheter during surgery.

SUMMARY OF INVENTION

The application of a minimally invasive surgical procedure to thoracic operations, particularly pulmonary resections, has been limited by fear of major hemorrhage, in the closed chest, of the pulmonary artery or vessels fed by it. Current methods of stopping hemorrhage would be greatly complicated by the lack of visibility at a closed operative site that results from uncontrolled vascular inflow to the artery. The present invention involves a method especially useful in thoracoscopic surgery and a catheter for practicing the method, for controlling hemorrhaging during surgery by precisely positioning an intravascular balloon at a point in a blood vessel which is effective to occlude blood flow to the surgical site. In its broadest aspect, the method involves trans-viewing a beacon on a catheter positioned inside of tissue near the operative arena.

In one aspect the catheter of the present invention is preferably a flow-directed catheter having an inflatable balloon located at its distal tip, and an inflation lumen for conducting fluid through the catheter for rapid inflation or deflation of the balloon. A light fiber extends through the catheter body to emit a beacon of light at a region positioned in the vicinity of the balloon. The light is relatively bright, and the emitted light is viewed from the surgical cavity, looking directly through the wall of the blood vessel to allow the position of the balloon in the vessel to be directly and quickly determined, thus simplifying and expediting balloon deployment in vivo.

In a preferred embodiment, the optical fiber is mounted in one lumen of a multi-lumen catheter, and receives light emanating from a light source which is coupled to an optical port located at the proximal end of the catheter. The fiber carries the light to one or more light emitting regions in the vicinity of the balloon. The locations of the light emitting regions are chosen like the running lights of a vehicle, to directly indicate the limits or extent of the balloon. Such sites, for example, may include small bands or points at the proximal and distal ends of the balloon, may include regions that extend for the entire length of the balloon, or may include combination of such positions. One light emitting region may be formed at the end of an optical fiber by simply fusing the end to melt it back into a clear luminescent sphere, a point-like termination approximately one millimeter in diameter which allows substantially all of the input light to escape omnidirectionally. The emitted light is of a brightness to be readily viewed through the corresponding blood vessel wall, but may be spectrally filtered, for example to be IR-free, to avoid excessive heating of the catheter, fiber or adjacent tissue while nonetheless having sufficient power to be readily seen. Alternatively, the emitted light may be of a wavelength that is not directly visible, but which is within the range of the endoscopic video camera and is clearly visible only in the video image. In this case, the wavelength may be selected to have a high tissue-penetrating range, allowing the emitters to be operated at a lower power level without sacrificing visibility. Thus, the endoscopic visual image is formed to include not only the surface tissue of the surgical arena, but one or more bright spots from the light emitters which lie in a vessel below the surface.

The catheter of the present invention preferably contains at least two lumens; namely, an inflation lumen for conducting fluid therethrough for rapid inflation or deflation of the balloon, and a lumen which carries the fiber. Additional lumens may be and preferably are supplied to fulfill other useful delivery or monitoring tasks. Such additional lumens may include a monitor lumen, extending through the catheter body distally past the balloon, which is used for carrying liquids to and from the proximal and distal ends of the catheter, as well as a proximal injectate lumen, which terminates at the proximal end of the balloon to supply heparin or other injectate to an outlet in that position. In general, only one or two such additional lumens may be supplied, due to the overall constraints on the size and stiffness of the catheter necessary to permit endovascular insertion.

As noted above, a thin optical fiber mounted in one lumen carries light from a light or source input located at the proximal end of the catheter to the light emitting region(s) in the vicinity of the balloon. In one configuration, the monitor lumen communicates with blood at the pulmonary arterial pressure when the catheter is in place and the balloon is deflated, or measures pulmonary capillary wedge pressure when the balloon is inflated. In another configuration, the monitor lumen is adapted at its proximal end for at least one of blood sampling or infusion of a therapeutic drug. As with the basic protocol described above for the first embodiment, by illuminating the light emitting region, the balloon is visually positioned in vivo.

In yet another embodiment, the light emitting balloon has at least one portion which inflates to a size and shape capable of occluding a blood vessel, and includes an anchor for immobilizing the balloon in the vessel before it is fully inflated. The anchor may be effected by a second portion of the balloon assembly which inflates to a shape or size that contacts the vessel, and without fully obstructing circulation, prevents movement of the balloon in a vessel.

In another aspect, the invention includes a method of preventing or controlling hemorrhage during minimally invasive thoracoscopic surgery by positioning a balloon to obstruct vascular inflow to the pulmonary artery or a branch thereof. According to this aspect, one or more incisions are made and an endoscope is inserted to view the surgical arena. The catheter of the present invention with its balloon deflated is inserted by cutdown or percutaneous insertion into a vein. The balloon is unfurled or partially inflated, and flow-directed through the heart and into the pulmonary artery on the side of the lung which is to be operated on. Prior to surgery, the catheter is then moved to the exact location of a relevant branch vessel by illuminating the fiber and observing the artery to see light emitted in the vicinity of the balloon. This "trans-viewing," or observation through the vessel tissue of the internal catheter beacon allows the exact location to be seen on the endoscope display screen. Surgery then proceeds, and in the event of accidental cutting of the pulmonary artery or of a secondary blood vessel during surgery, the already-positioned balloon is rapidly inflated to occlude the relevant supply vessel, thus stopping blood flow and making it possible to proceed with surgical closure of the bleed. The method disclosed herein is preferably applied to pulmonary resections including, but not limited to, lobectomy, bilobectomy and pneumonectomy.

Furthermore, it is contemplated that the method disclosed herein can be more generally applied to control vascular flow to and from any blood vessel, e.g., arteries and veins, during other minimally invasive surgical procedures including, but not limited to, laparoscopic, endoluminal, perivisceral, intra-articular and other endoscopic surgical procedures, as well as hybrid procedures. More specifically, the disclosed catheter can be targeted to a major blood vessel feeding into an operating site and its exact location is directly visualized using an endoscopic camera by illuminating the fiber and observing the light emitted in the vicinity of the balloon. Much as described for the example of the pulmonary artery in thoracoscopic surgery, in the event of an accidental injury during surgery, the balloon is rapidly inflated to prevent blood entry into the operative site, and thus provide a blood-free area in which to operate, or close a bleed.

The advantages of the present invention include the direct determination of the exact location of a catheter tip in vivo, without cumbersome radiographic procedures or expensive imaging equipment, thus allowing the rapid and dependable deployment of the catheter at a precise site to be ready if needed during surgery. Furthermore, the efficiency of pressure monitoring, blood sampling or drug infusion processes may be enhanced by allowing the placement of the catheter with greater precision and speed.

BRIEF DESCRIPTION OF THE DRAWINGS

These and other objects and advantages of the invention will be apparent from the specification and the drawings of illustrative embodiments, wherein.

DETAILED DESCRIPTION OF THE INVENTION

Figure 1:
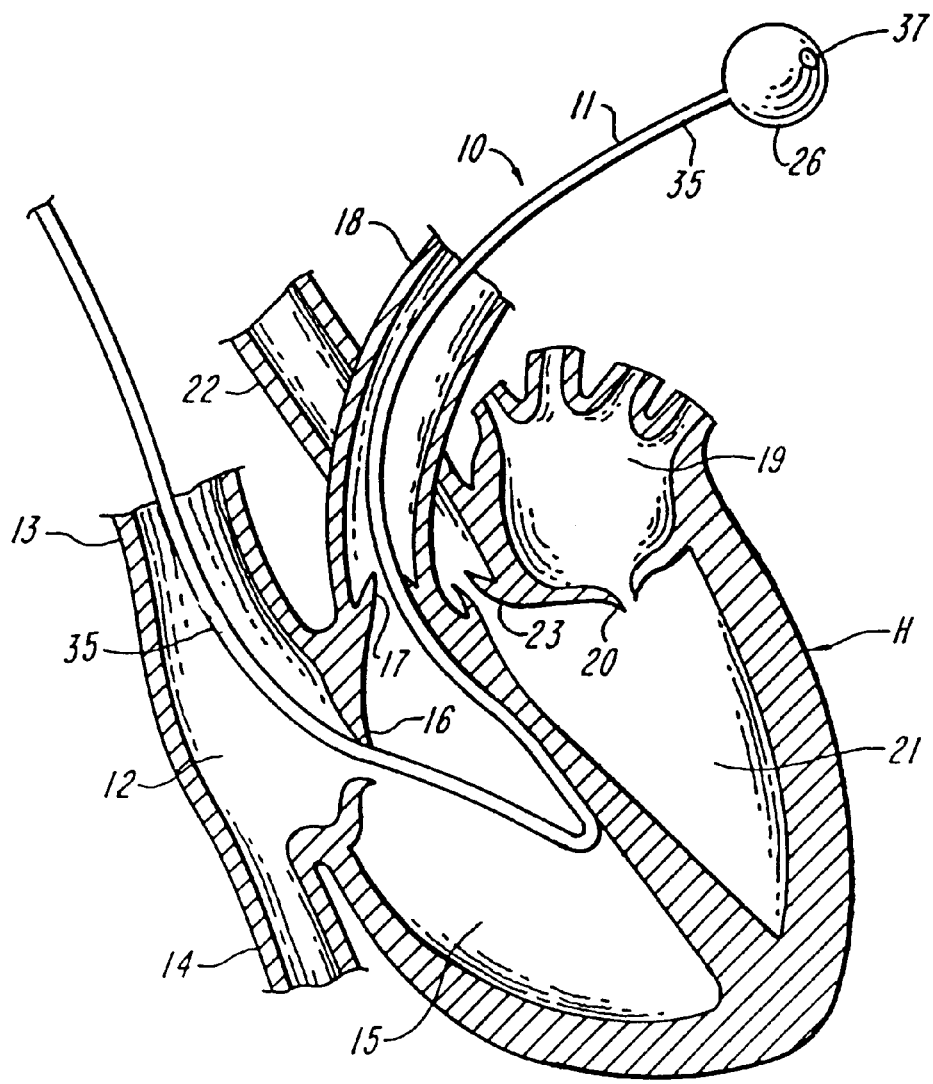
FIG. 1 is a diagrammatic sectional view illustrating a flow-directed catheter of this invention positioned in the pulmonary artery.

FIG. 1 illustrates a catheter 10 extending to the right side of a patient's heart H. In brief, the parts of the heart and their operation are as follows: the right atrium 12 receives blood from the superior and inferior vena cava 13 and 14, respectively, and pumps the received blood into the right ventricle 15 through the tricuspid valve 16. From the right ventricle, the blood travels through the pulmonary valve 17 and to the pulmonary artery 18 and on to the lungs. Oxygenated blood returning from the lungs enters the left atrium 19 and then passes through the mitral valve 20 into the left ventricle 21, which pumps blood out of the heart through the aortic valve 23 along the aorta 22. The pulmonary artery 18, while indicated as a single vessel, in fact branches close to the heart, with one passage going to the left lobe of the lungs and another going to the right lobe.

Figure 2:
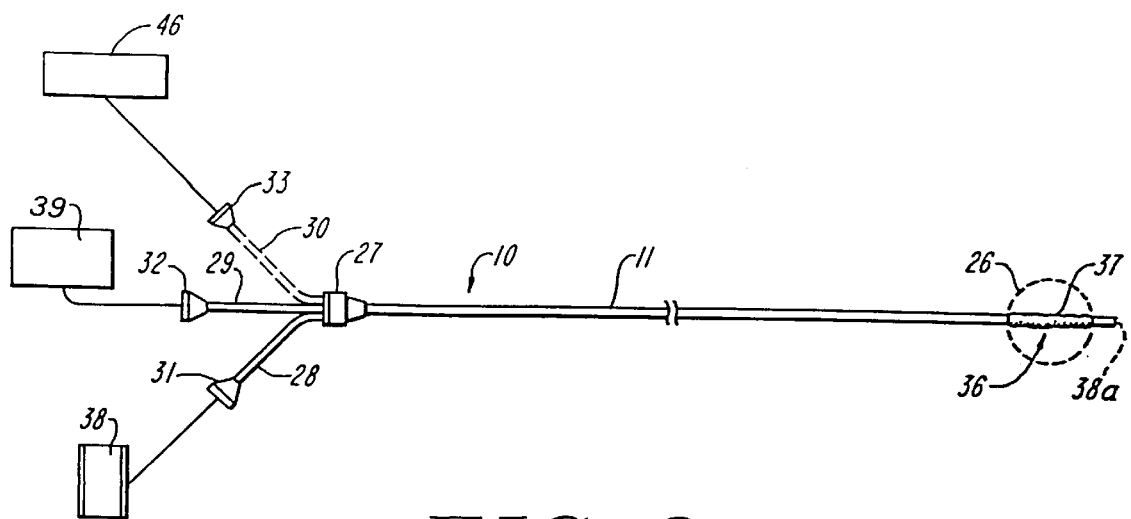
FIG. 2 is a side elevational view of the catheter.

Catheter 10 is depicted in FIG. 2 as a flow-directed catheter having a thin, flexible, tubular body 11 and an inflatable balloon 26 attached to its distal end. The balloon is shown in a fully deflated and in a fully inflated condition (dashed lines) in FIGS. 2A and 2B, respectively. The diameter of the catheter varies depending on its desired use; however, the diameter is typically in the range of about 4 to 12 French (0.052 inch to 0.156 inch). Most preferably the catheter diameter is in the range of about 4 to 7 French (0.052 to 0.091 inch). Exemplary catheter constructions are disclosed in U.S. Pat. Nos. 3,746,003, 3,833,004, 3,710,781, 3,634,924, 3,152,592, 3,044,468, 3,050,066 and 2,845,930, each of which is incorporated by reference herein.

For completeness, it is noted here that by "flow-directed", applicant means that the preferred balloon insertion process relies, at least in part, on the pressure of blood flow against the balloon to drive the balloon along, pulling the trailing catheter after it. Thus, unlike a relatively rigid angioplasty catheter that employs a deflated strong elastic balloon which is pushed along on a guide wire, or pushed by a stiff tube, the catheter contemplated by applicant employs a relatively flaccid and partly enlarged balloon, and a light, flexible catheter capable of bending freely to follow the balloon when blood flow propels the balloon along a turning path through the heart.

Continuing with a description of FIG. 2, at its proximal end, the catheter body 11 terminates in a coupling 27, typically a short handle assembly, which operably connects the lumens of the catheter to connector tubes or lines 28, 29 and 30. All of these tubes or lines contain coupling elements 31–33 of appropriate type for attaching the connector lines to syringes, sampling instruments and other devices. In an illustrative embodiment, connector line 28 is operably attached through coupling element 31 to a balloon inflation unit 38 which pumps or injects fluid for rapid inflation or deflation of balloon 26; connector 29 is operably connected through a standard fiber optic coupler 32 to a light source 39; and optional connector tube 30 (shown in dashed lines) is attached via coupling element 33 such as a Luer connector to a monitor system 46 which for example includes instrumentation for at least one of pressure monitoring, blood sampling, and infusion of a therapeutic drug. Light source 39 may be any suitable light source. One such source may be a small battery-powered source having 5–10 W power consumption and emitting broadband visible light, such as a 6 W white light having an elliptical reflector configured to focus the light into a fiber for delivery via coupler 33. Another suitable source may be realized by coupling light from a standard 200 watt Xenon surgical endoscopic camera lighting unit. In this case, the standard source is preferably modified so that its outputs partitioned between two optical ports, one for the endoscope and one for the catheter lights. In general a luminous flux of about 20–100 lumens is considered sufficient for the powering the fiber(s) of the catheter, representing approximately one to ten percent of the video illumination light. The partition may be readily achieved by a simple split-area Y-junction light guide or by other available optical hardware. The source ports may further be equipped with controls for dimming or blanking each output independently so that the illumination of the catheter can be viewed against a dimmed or unsaturated video image.

In accordance with a principal aspect of the present invention, the light provided to the balloon catheter is emitted at or near the balloon and serves as a visual aid to mark the location of the balloon at the catheter tip. For this reason, broadband white light is the preferred light for source 39. However, for application in minimally invasive surgery when an endoscopic video camera is used, the video camera may have a wavelength sensitivity greater than, or different than the human eye, and in that case in addition to white light, the invention may employ light of a specific wavelength, for example a wavelength to which the camera responds even if it would not be directly visible without detection by the camera. Further, the wavelength may be selected based on desirable characteristics, such as its ability to penetrate a vessel without absorption, or to provide a color contrast to the background tissue, or a similar property. It should be noted that in general a filter is provided to remove infrared (IR) light ahead of the camera to decrease the overall background noise. Thus, if an infrared wavelength is used to illuminate the beacon on the balloon it must be a narrow-band IR, preferably below one micrometer, and may be separated for detection, by a dichroic mirror or beam splitter, so that the rest of the image is not impaired. The light source may also be controlled to automatically dim or extinguish the general endoscope illumination when illuminating and viewing the balloon beacons, to enhance their visibility.

Figure 3:
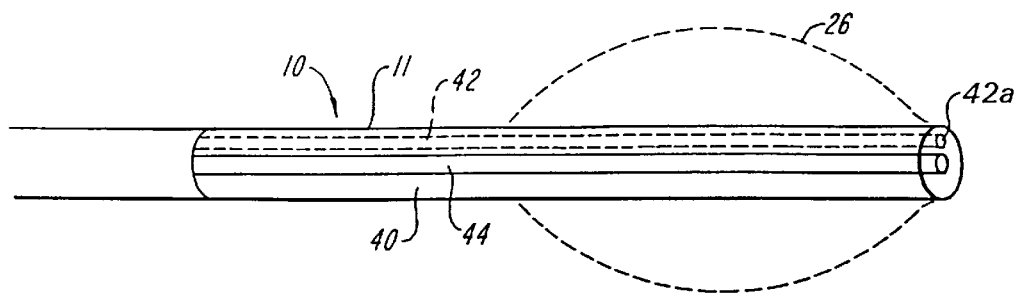
FIG. 3 is an enlarged side sectional view of the distal end of the catheter when the balloon is inflated.

FIG. 3 shows an enlarged side sectional view of the distal end of the catheter body 11. Inflation lumen 40 is a passage extending through the catheter body 11 which communicates with connector tube 28 and conveys gas or another inflation medium to and from the balloon inflation unit 38 (FIG. 2).

Inflation lumen 40 has a distal opening, or port 37 (FIGS. 2A, 2B) which may for example consist of a number of holes opening into the interior of balloon 26 for a fluid flow therethrough to rapidly inflate and deflate said balloon. Light fiber 42 is mounted in the inflation lumen or an adjacent lumen and extends longitudinally through said lumen (dashed lines). Fiber 42 carries light from light source 39 distally through the lumen to one or more emission regions 36, examples of which are shown in FIGS. 2A–B and 4B–C. In one embodiment, monitor lumen 44 operably connects to monitor system 46 via port 33 and connector tube 30. This lumen carries liquids, e.g., therapeutic drugs, blood, to or from the proximal and distal ends of the catheter. Syringes and other devices can be attached to monitor system 46 by methods known in the art.

Figure 4A:
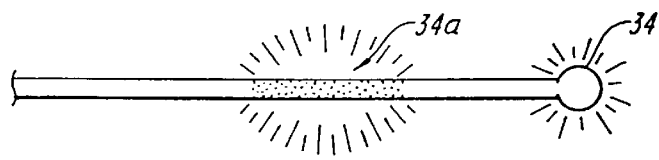
FIG. 4A is a schematic representation of direct emission regions of an optical fiber.
Figure 4C:
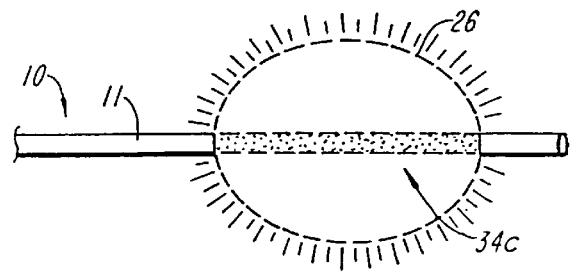
FIGS. 4B and 4C are enlarged side elevational views of the distal end with the catheter illuminated and the balloon inflated showing alternative positions of light emitting regions at the ends of the balloon (FIG. 4B) or along the balloon length FIG. 4C)
Figure 4B:
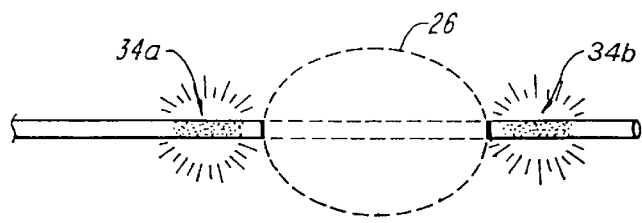

At the distal end of catheter 10 in the vicinity of balloon 26, the fiber 42 is coupled to one or more emitter regions 36 that emit light detectable through the walls of a blood vessel (FIGS. 4B and 4C). FIG. 4A depicts a thin optical fiber which has a core diameter ranging from 150 to 600 microns, most preferably in the range of about 300 to 500 microns. A high numerical aperture fiber is used to provide effective light transmission at a sufficient intensity to be remotely visible. The light source may include an IR filter to avoid applying excessive heat while nonetheless passing sufficient power to be readily visualized through the blood vessel without damaging the tissue therein. Light travels from light source 39 through the optical fiber to substantially entirely escape and project omnidirectionally at the light emitting regions 36 in the vicinity of the balloon (FIGS. 2 and 3). A light emitting region may be formed by fusing the end of the optical fiber to form a luminescent ball 34, FIG. 4A. Alternatively, or in addition, one or more light scattering regions 34a, 34b and 34c (FIGS. 4A–C) may be formed directly in the fiber by etching away the fiber cladding and roughening the surface of the fiber in local areas using an acid treatment or reactive etch methods known in the art or by coupling the fiber to a roughend transparent tube segment or the like. Alternative locations of the emitter regions 36 along the longitudinal axis of the catheter body 11 are contemplated in the present invention. The light emitting region can be positioned at the proximal end 34a, distal end 34b or the entire length 34c of the balloon 26 (FIGS. 4B and 4C). Any combination of these configurations is within the scope of the present invention. In addition, by placing different colored filters at the light emitting regions 34a–34c, an emitted pattern of light of different colors can provide a visible indication of precisely which part of the balloon is being viewed through the blood vessel wall. Several different light guides, for example a pair of 300 micron fibers, may be used to illuminate the different areas. Furthermore the light emitters may be positioned at radially outward positions, or extend as protrusions so that the optical path absorbance through blood to the outside is reduced, enhancing visibility.

Figure 2A:
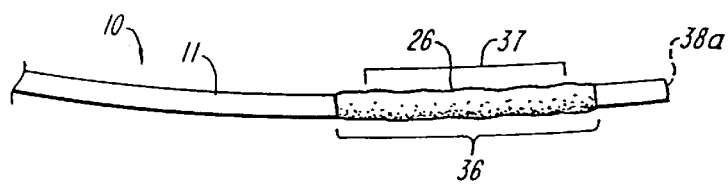
FIGS. 2A and 2B are enlarged side elevational views of the distal end of the catheter with the balloon in a deflated or inflated configuration, respectively.
Figure 2B:
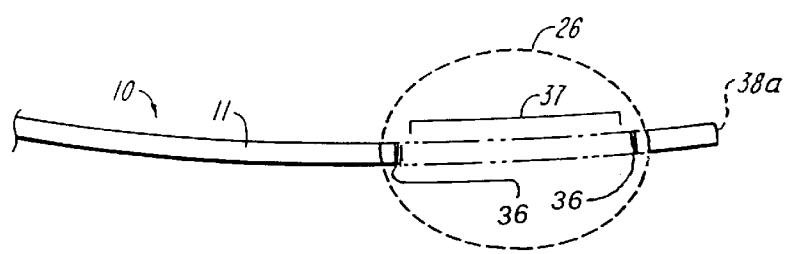

The inflation openings 37 and monitor port 38a located at the distal end of catheter 10 operably connect the lumens of the catheter to the balloon interior and to the exterior vessel region, respectively (FIGS. 2, 2A and 2B). Port 37 is a lateral opening formed in the wall of the catheter body 11 to allow fluid flow therethrough for inflation and deflation of balloon 26. The monitor port 38a is located at the tip of the catheter body 11 distal to the balloon 26. When the catheter is properly positioned into the pulmonary capillary wedge position, port 38a may be used for measuring pulmonary artery or pulmonary capillary wedge pressure. Alternatively, port 38a may be used for injecting or infusing solutions, or for taking blood samples. The invention also contemplates an additional fluids port (not shown) located proximally of the balloon.

Figure 5A:
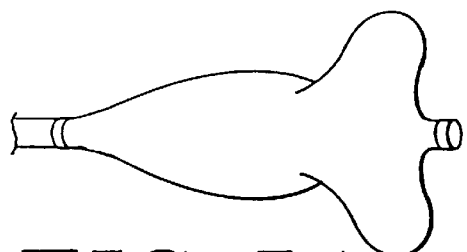
FIGS. 5A and 5B are diagrams of different balloon shapes for a balloon catheter of the present invention.
Figure 5B:

FIGS. 5A and 5B illustrate another embodiment of the present invention, wherein balloon 26 has plural segments or at least partially distinct body portions. These contain at least one portion which inflates to a size and shape capable of occluding, without necessarily distending, a blood vessel and a possibly different portion for stabilizing the balloon in position. In one configuration, inflated balloon 26 has two differently shaped portions consisting of a cylindrical shaped occlusion portion connected to a second separate portion that inflates to contact a blood vessel in at least two points (FIG. 5A) and anchor the assembly, but does not fully occlude the vessel lumen. The cylindrical inflated shape may more generally be a configuration where the largest diameter in a plane transverse to the long axis of the balloon is located intermediate the ends of the balloon, and the balloon diameter decreases in both directions toward the ends. This portion of the balloon inflates to a shape and size that occludes a blood vessel. The second portion anchors the balloon within the blood vessel by inflating to a crossbar, a long curve, projecting fingers or a star-like shape, or other shape contacting the walls of the vessel sufficiently to anchor the assembly without occluding blood flow. In another configuration, the balloon has the above-described cylindrical inflated shape (FIG. 5B) but may, for example, be fabricated so it will curve longitudinally before expanding radially, or so that it otherwise wedges in position before occlusion, ready to fully inflate. The balloon size can be easily adapted for use in humans or non-human animals, e.g., pigs. The balloon may also be secured in place using any of the attachment methods known in the art, for example as shown in U.S. Pat. Nos. 3,995,623, 3,746,003 and 3,833,004. Mechanical anchoring devices, such as hooks or the like which are activated from the catheter handle, may be used to anchor the balloon in which case a single inflatable balloon, body shaped like that of a conventional Swan-Ganz catheter is used.

The inflation medium can be selected from any type of biocompatible fluid, preferably in gaseous form so that it pumps quickly through the catheter and has a fast response time, and preferably also being a material having rapid absorption in the blood, so as to reduce the possibility of injury in the event of balloon rupture. Carbon dioxide is a preferred inflation medium; however, other gases may be used under special circumstances.

Alternative methods of mechanically anchoring the balloon in a blood vessel are also envisioned in the present invention. These may include physically clamping the balloon by having a mechanically activated clamp or stent structure incorporated into the catheter end, or by surgically applying a partially constricting clamp or clip around the vessel in the surgical cavity to grip the balloon tip enough to prevent balloon migration along the vessel. Another method includes attaching a magnetic fragment to the balloon, and then locking the balloon in place in a blood vessel using an external magnet. In that case the external magnet is manually positioned against the vessel wall to hold the balloon fixed. The external magnet may, for example, be attached to the end of a rod or wand. In this embodiment the magnetic wand may also be used to steer the catheter to the correct pulmonary branch once it has passed through the right ventricle.

Figure 6:
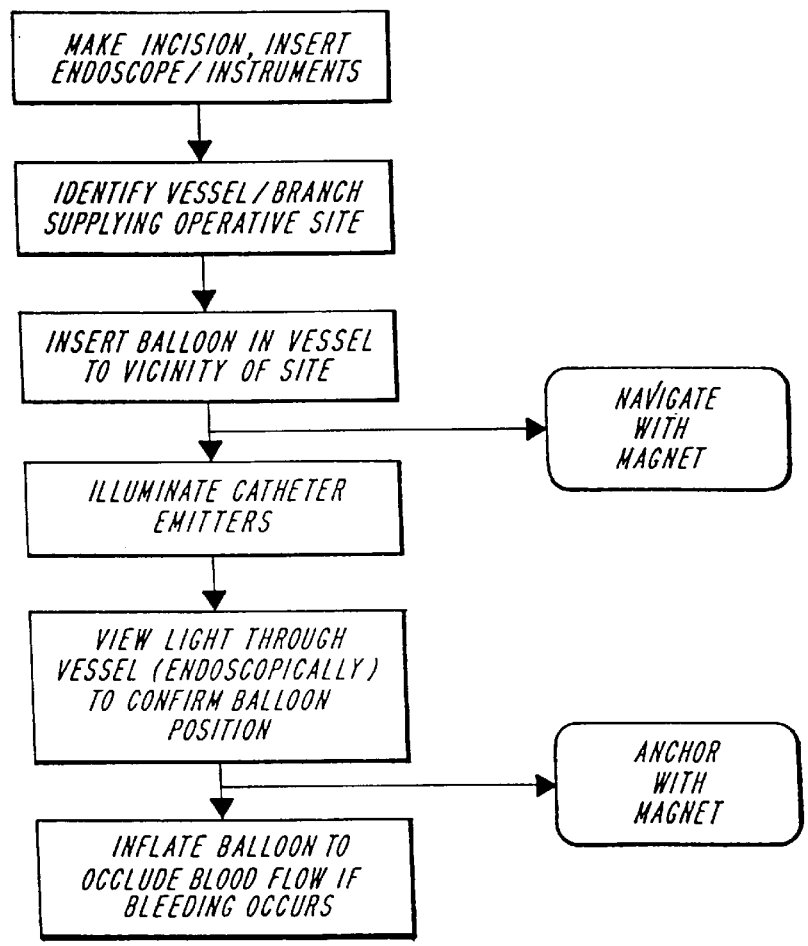
FIG. 6 is a flow-chart illustrating the steps in the method of the invention.
Figure 7:
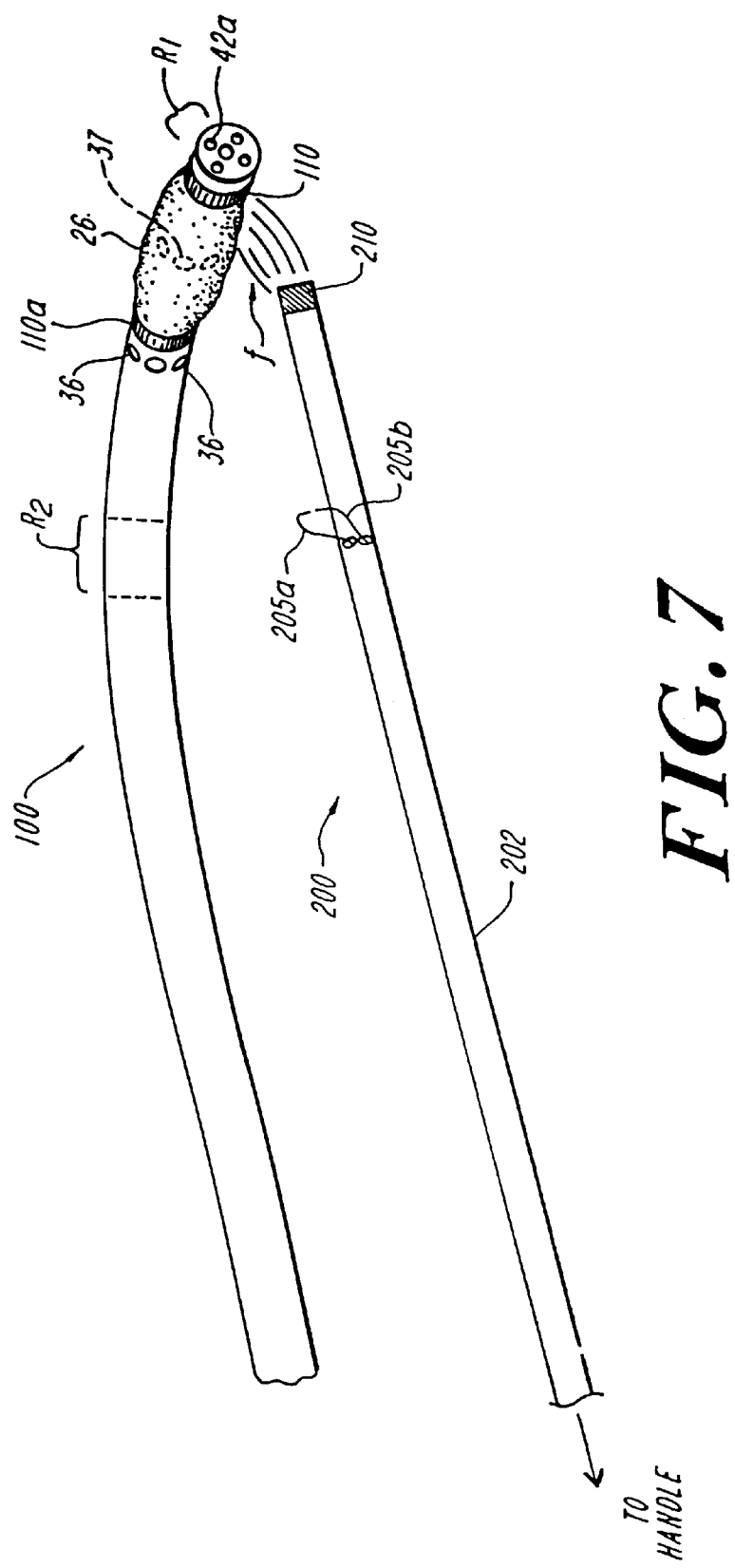

In another aspect, the present invention includes a surgical method for preventing or controlling hemorrhage in an enclosed surgical arena. FIG. 6 shows steps of this method.

In an illustrative embodiment, a method is applied to obstruct vascular inflow to the pulmonary artery during minimally invasive thoracoscopic surgery. The method disclosed herein is preferably applied to pulmonary resections including, but not limited to, lobectomy, bilobectomy and pneumonectomy. In use, the soft, pliable catheter 10 having the balloon in a deflated configuration is inserted into a patient's median basilic or deep brachial vein by a cutdown, or it may be inserted percutaneously via the femoral, jugular or subclavian vein. Alternatively, the pulmonary artery may be accessed more directly from the chest. The catheter is then advanced by blood flow with or without fluoroscopic visualization into the right atrium 12 and right ventricle 15 and advanced to the branch of the pulmonary artery on the side of the lung which is to be operated on (FIG. 1). Prior to surgery, the balloon is moved to the exact location by illuminating its fiber and observing directly or through an endoscopic camera the light emitted in the pulmonary artery in the vicinity of balloon (FIGS. 4B and 4C). The catheter may be pulled back slightly and reinserted to the correct branch, or may be steered with a magnetic wand as described above, to the location, and the balloon is anchored in this position. In the event of accidental puncture of the pulmonary artery or a downstream blood vessel during surgery, the balloon is then rapidly inflated to occlude the pulmonary artery, thus stopping blood flow, and allowing the cut to be stapled or otherwise closed.

In an experimental protocol using a prototype illuminated catheter, pulmonary artery blood flow has been interrupted intermittently in medium sized pigs using the catheter described in the present invention. The domestic pig was chosen as the experimental model because the porcine lung anatomy has well-defined lobar structure. Moreover, the pig has a defined distribution and branching of the pulmonary artery, the pulmonary veins and the bronchial system. The procedure was as follows. Briefly, a young adult pig (50–75 pounds) was anesthetized and airway intubated. Pulse rate, heart rhythm and blood pressure were monitored by conventional methods. Under fluoroscopic control the balloon catheter was flow directed into the branch of the pulmonary artery feeding into the surgical lung. A 3 cm-long cylindrical balloon was used. This balloon size has been tested to occlude, without overdistending, the porcine pulmonary artery. The animal was then placed in the thoracotomy position and the necessary thoracoscopic surgery port incisions, each approximately 2 cm in length, were created. An endoscopic camera and instruments were inserted. The proper location of the balloon was determined by viewing the light emitted in the vicinity of balloon, using the endoscopic camera. Inflation of the balloon interrupted blood flow into the operated lung allowing a blood-free area in which to perform lung surgery, e.g., pulmonary lobectomy, bilobectomy and pneumonectomy.

In another embodiment, this invention includes an improved method for monitoring blood pressure or sample infusion by directly determining the exact location of a catheter in vivo. With the catheter in the proper position, a variety of diagnostic procedures may take place, all of which are known in the art, and will only be described briefly here. For example, monitor port 38a may be used for measuring pulmonary artery and pulmonary wedge pressure by positioning the catheter into what is generally referred to as the pulmonary capillary wedge position. Monitor lumen 44 communicates with blood at the pulmonary arterial pressure when the catheter is in the wedge position and the balloon is deflated, or pulmonary capillary wedge position when the balloon is inflated. Pressure measurements are detected using monitor system 46. Alternatively, port 38a may be used for fluid sampling or injection of a therapeutic drug by attaching a syringe, containing such a fluid or drug, to the connector tube 30.

The invention may also be practiced during operations involving an open surgical arena. In that case the position of the balloon is determined by direct visual observation of the light emission through tissue or a vessel in the operating site. In this case, the location of an endovascular balloon for hemostasis offers an improvement in speed and dependability for emergency hemostasis. As further noted above, while the pulmonary artery is relatively transparent, the invention is expected to work equally well for other tubes, passages or vessels in laporoscopic and other applications.

Thus, although the invention has been extensively described with respect to a balloon-tipped catheter and a novel method of use to control hemorrhage during minimally invasive thoracscocopic surgery, it is understood that the invention is applicable to all surgical procedures wherein an illuminated balloon catheter viewed through the walls of a blood vessel is used to occlude a vessel supplying the site of surgery. Furthermore, in its full generality, the method of locating a hemostatic balloon by directly viewing a fiber-optic beacon, may be applied more generally to locate the distal tip of a catheter, even when no balloon is present. Thus, the invention contemplates positioning the tip of a drug delivery catheter, an ablation catheter, an endoluminal paving catheter, or other internally-positioned surgical device by constructing the catheter or other device with a light pipe or optical fiber to conduct light to one or more emitting beacons located to identify the active portion of the catheter, such as a drug delivery port, a stent delivery segment or a sampling inlet or biopsy cup, and then positioning the device in a passage by such illumination and trans-viewing. Further, various modifications may be made to the invention described herein without departing from the intended, scope of the invention, as set forth in the claims appended hereto.

What is claimed is:

1. A catheter apparatus for controlling hemorrhage in an enclosed surgical arena, said apparatus comprising a flexible catheter body configured for travel within a blood vessel extending to the surgical arena by percutaneous insertion or cutdown to access a site in the vessel, said catheter body including an elongated tubular wall having proximal and distal ends, and having at least an inflation lumen and an optical fiber extending between said ends, said fiber being configured for coupling to receive light at the proximal end and guide light to the distal end, and said fiber being configured at said distal end as a beacon which emits said received light through the wall of the vessel as a precise position marker visible externally of the vessel wall for allowing positioning of said catheter distal end in the vessel, and a balloon secured at said distal end of the flexible catheter body and inflatable via said inflation lumen, said balloon being configured for travel with said flexible catheter along the blood vessel, said inflation lumen having a distal opening into said inflatable balloon for providing a fluid flow for rapid inflation and deflation of the balloon, whereby, when precise position of the balloon within a blood vessel is visually confirmed by viewing said beacon, the balloon is disposed for inflation to occlude blood flow and prevent hemorrhage in an identified region of the surgical arena, and magnetic material secured to said balloon for magnetic engagement and positioning of the balloon by manipulation of a magnet located outside the blood vessel.

2. The catheter apparatus of claim 1, further comprising a monitor lumen having proximal and distal ends which extends completely through the catheter body distally past said balloon to communicate with blood in the vessel for measuring pulmonary arterial pressure when the catheter is in place and the balloon is deflated, and for measuring pulmonary capillary wedge pressure when the balloon is inflated.

3. The catheter apparatus of claim 2, wherein the proximal end of said monitor lumen is configured for at least one of blood sampling and infusion of a therapeutic drug.

4. The catheter apparatus of claim 1, wherein the fiber emits light in a band which is directly visible or within the spectral band of a video camera.

5. The catheter apparatus of claim 1, wherein the fiber is configured to emit light at one or more regions selected from the distal end, the proximal end, the entire length of said balloon, and combinations thereof.

6. The catheter apparatus of claim 1, wherein the balloon includes a portion having a generally cylindrical inflated shape with a largest diameter in a plane transverse to the long axis of said cylinder and located intermediate the ends of said cylinder, and a balloon diameter which decreases in both directions along said axis.

7. The catheter apparatus of claim 1, wherein the balloon includes at least a first portion which inflates to a size to occlude the blood vessel and a second portion which inflates to a size effective to contact the vessel and anchor the balloon with a shape that leaves a passage in the vessel open, so that the balloon is thereby configured, upon inflating the second portion and not the first portion, to anchor within the vessel without fully obstructing circulation therein.

8. The apparatus of claim 1, wherein said balloon has a size to occlude circulation in a blood vessel selected from among the thoracic, liver and abdominal vasculature.

9. The catheter apparatus of claim 1, wherein the catheter is a flow-directed catheter in which the balloon is entrained by flow to carry the catheter to an operative position.

\* \* \* \* \*